(12) United States Patent
Brunelle et al.

(10) Patent No.: US 6,479,658 B1
(45) Date of Patent: Nov. 12, 2002

(54) METHOD FOR CYCLIZING HYDROLYSIS OF AN AMINONITRILE COMPOUND INTO LACTAM

(75) Inventors: Jean-Pierre Brunelle, Croissy-sur-Seine (FR); Aline Seigneurin, Le Chesnay (FR); Lionel Sever, Lyons (FR)

(73) Assignee: Rhodia Fiber & Resin Intermediates, Courbevoie Cedex (FR)

( * ) Notice: Subject to any disclaimer, the term of this patent is extended or adjusted under 35 U.S.C. 154(b) by 0 days.

(21) Appl. No.: 09/744,210
(22) PCT Filed: Jul. 15, 1999
(86) PCT No.: PCT/FR99/01730
§ 371 (c)(1), (2), (4) Date: Jun. 4, 2001
(87) PCT Pub. No.: WO00/05203
PCT Pub. Date: Feb. 3, 2000

(30) Foreign Application Priority Data

Jul. 22, 1998 (FR) ............................................. 98 09529

(51) Int. Cl.⁷ ..................... C07D 223/08; C07D 201/02
(52) U.S. Cl. ....................................... 540/485; 540/534
(58) Field of Search .................................. 540/485, 534

(56) References Cited

U.S. PATENT DOCUMENTS

| 2,357,484 A | * 9/1944 | Martin et al. ................ 260/239 |
| 4,625,023 A | * 11/1986 | Mares et al. ................ 540/539 |
| 4,628,085 A | * 12/1986 | Mares et al. ................ 540/539 |

FOREIGN PATENT DOCUMENTS

| DE | 196 32 006 A | 2/1998 |
| EP | 0 748 797 A | 12/1996 |
| WO | 96 22974 | 8/1996 |

* cited by examiner

*Primary Examiner*—T. A. Solola
*Assistant Examiner*—Golam M M Shameem
(74) *Attorney, Agent, or Firm*—Burns, Doane, Swecker & Mathis, L.L.P.

(57) ABSTRACT

The invention relates to a process for the cyclizing hydrolysis of an aminonitrile compound into a lactam in the presence of a catalyst.

The invention relates more particularly to a process for the cyclizing hydrolysis of an aminonitrile compound in the presence of a macroporous particulate catalyst obtained by deposition/impregnation of an oxygenated compound onto a macroporous support such as alumina. The invention applies in particular to the preparation of $\epsilon$-caprolactam by cyclizing hydrolysis of aminocapronitrile.

13 Claims, No Drawings

METHOD FOR CYCLIZING HYDROLYSIS OF AN AMINONITRILE COMPOUND INTO LACTAM

This application is a 371 of PCT/FR99/01730 Jul. 15, 1999.

The invention relates to a process for the cyclizing hydrolysis of an aminonitrile compound into a lactam in the presence of a catalyst.

The invention relates more particularly to a process for the cyclizing hydrolysis of an aminonitrile compound in the presence of a macroporous particulate catalyst obtained by deposition/impregnation or adsorption of an oxidized compound onto a macroporous support.

Lactams, such as ε-caprolactam, are base compounds for the manufacture of polyamides and in particular PA 6.

Among the various known processes for synthesizing these lactams, one of the processes is the cyclizing hydrolysis of the corresponding aminonitrile, and more particularly of a corresponding aliphatic aminonitrile, in the presence of water and a catalyst.

Thus, U.S. Pat. No. 2,357,484 describes a process for the vapour-phase preparation of lactam, with activated alumina, silica in gel form or borophosphoric acid as catalyst.

U.S. Pat. No. 4,628,085 also describes a process for preparing lactams by vapour-phase cyclizing hydrolysis in the presence of a silica-based catalyst with a specific surface of greater than 250 m²/g. This reaction is performed in the presence of hydrogen and ammonia.

Patent application WO 98/0669 proposes catalysts based on hydrated or non-hydrated metal oxides, the metals being chosen from the group comprising tin, zirconium, hafnium, bismuth, vanadium, niobium and tantalum or mixtures thereof. These catalysts are of bulk type and have no macroporosity. Their cycle time is very short and incompatible with an industrial exploitation of the lactam manufacturing process.

a process for the vapour-phase cyclizing hydrolysis of aminonitrile using, as catalyst, an alumina which has domains of determined specific surface and pore volume.

The lactams produced are generally used for the manufacture of polymer, such as, for example, ε-caprolactam for the manufacture of PA 6. The applications of these polymers are many and varied.

However, one of the most important applications is the manufacture of yarns, filaments or fibres in particular for the textile industry.

These varied applications, and in particular the one described above, require the use of a polyamide which has very specific physicochemical and chemical properties. To obtain such properties, it is necessary to synthesize these polymers from monomers or lactams which also have very strict purity properties.

Thus, the caprolactam must generally satisfy the following specifications:

permanganate index (according to ISO standard 8660): <5 free bases: <0.1 milliequivalent (meq)/kg of CPL volatile bases (according to ISO standard 8661): <0.5 meq/kg UV absorbance at 290 nm (according to ISO standard 7059): <0.05

To obtain these specifications, it is necessary to carry out complex purification processes. Such processes have many economic drawbacks, in particular large energy consumption and heavy investment in materials.

One of the reasons for the need to purify the crude lactam produced by the known processes is the presence of side reactions which arise in particular during the step of cyclizing hydrolysis of the aminonitrile.

To avoid these side reactions, it is thus necessary for the catalyst to promote the main reaction of formation of the lactam. This property of the catalyst can be illustrated by the selectivity of the process towards crude lactam. The quality of crude lactam can also be assessed by titrating it with an aqueous 0.2 N potassium permanganate solution (permanganate index).

In addition, in order for the purity of the crude lactam produced to be high and continuous, it is necessary for the level of selectivity of the catalyst to be conserved throughout the catalyst's cycle time.

The aluminas proposed in the Applicant's patent application WO 96/22974 represents the start of a solution to this problem by proposing a highly active and selective catalyst which has a long cycle time.

However, it appears necessary to further improve the performance levels of the catalysis for the cyclizing hydrolysis of lactams, in order to improve the initial selectivity of the catalyst as well as the purity of the crude lactam, while at the same time maintaining this high level throughout the catalyst's cycle time.

One of the aims of the present invention is to propose a solution for improving the catalysis for the cyclizing hydrolysis of aminonitriles, and in particular the selectivity of this catalysis to produce a crude lactam in a high degree of purity. Thus, the crude lactam produced can be used for the manufacture of polymer with high chemical and physicochemical properties, after carrying out a purification process which is simpler and more economical than those currently used.

The expression "crude lactam" refers to the product from the cyclizing hydrolysis reaction after removal of the ammonia and any solvents such as water, for example.

The expression "purified lactam" denotes the lactam obtained by purification of the crude lactam.

To this end, the invention proposes a process for the cyclizing hydrolysis of an aminonitrile compound into a lactam by reaction of an aminonitrile of general formula (I) below:

$$N{\equiv}C{-}R{-}NH_2 \qquad (I)$$

in which:

R represents a substituted or unsubstituted aliphatic, cycloaliphatic or arylaliphatic radical comprising from 3 to 12 carbon atoms, with water, in the presence of a solid catalyst, characterized in that the catalyst is a particulate catalyst obtained by deposition and/or adsorption of at least one oxygenated compound of at least one element chosen from the group consisting of the elements belonging to groups 1 to 16 of the universal classification of the elements (new classification), this list also including rare-earth metals, on a particulate support made of simple or mixed inorganic oxide of at least one element chosen from the group consisting of silicon, aluminium, titanium, zirconium, vanadium, niobium, tantalum, tungsten, molybdenum, iron and rare-earth metals, or by mixing together at least one of the said oxygenated compounds or a precursor of the said oxygenated compounds with the inorganic oxide(s) forming the support before shaping them.

According to the invention, the particulate catalyst comprises at least one macroporosity characterized by a pore volume, corresponding to pores greater than 500 Å in diameter, of greater than or equal to 5 ml/100 g.

This macroporosity is advantageously formed during the process for shaping the particles by the techniques described below, or like, for example, the addition of porogen.

The catalyst can be used in various forms, such as beads, grindings, extrudates in the form of hollow or solid cylindrical granules, honeycombs or pellets, the shaping optionally being carried out using a binder.

They can be, firstly, beads of inorganic oxides derived from an oil-drop shaping (or drop coagulation). Beads of this type can be prepared, for example, by a process similar to the one described for the formation of alumina beads in patents EP-A-0,015,801 or EP-A-0,097,539. Control of the porosity can be achieved in particular, according to the process described in patent EP-A-0,097,539, by drop coagulation of an aqueous suspension or dispersion of inorganic oxide.

The beads can also be obtained by a process of aggregation in a rotating drum or granulator.

They can also be extrudates of inorganic oxides. These can be obtained by blending and then extrusion of a material based on the inorganic oxide. Controlling the porosity of these extrudates can be achieved by the choice of oxide used and by the conditions for preparing this oxide or by the conditions for blending this oxide before extrusion. The inorganic oxide can thus be mixed with porogens during the blending. By way of example, the extrudates can be prepared by the process described in U.S. Pat. No. 3,856,708.

Similarly, beads of controlled porosity can be obtained by addition of porogen and aggregation in a rotating bowl or granulator or by the "oil drop" process.

These shaping processes can be carried out by using a mixture of the inorganic oxide and an oxidized compound in accordance with the invention, or a precursor of the said oxygenated compound, the precursor being converted into oxidized compound by heat treatment of the catalyst, for example, and advantageously after shaping.

According to another characteristic of the invention, the catalyst particles have a specific surface of greater than 10 m$^2$/g and a pore volume of greater than or equal to 10 ml/100 g, the pore volume corresponding to pores greater than 500 Å in diameter being greater than or equal to 10 ml/100 g.

According to another characteristic of the invention, the catalyst particles have a specific surface of greater than 50 m$^2$/g.

Advantageously, they have a total pore volume of greater than or equal to 15 ml/100 g with a pore volume corresponding to pores greater than 200 Å in diameter of greater than or equal to 15 ml/100 g, preferably greater than or equal to 20 ml/100 g.

According to another characteristic of the invention, the catalyst has a total pore volume of greater than or equal to 20 ml/100 g with a pore volume corresponding to pores greater than 70 Å in diameter of greater than or equal to 20 ml/100 g.

In the procedure comprising a porous support supporting oxygenated compounds of elements, these elements are advantageously chosen from the list comprising silicon, titanium, zirconium, vanadium, niobium, tantalum, tungsten, molybdenum, phosphorus, boron, iron, alkaline-earth metals and rare-earth metals. The oxygenated compound is advantageously a simple or mixed oxide of one or more of the elements mentioned above or a mixture of these oxides.

In this embodiment, the porous support is preferably a porous alumina. Advantageously, this alumina has the specific surface, pore volume and pore distribution properties defined above.

This embodiment is particularly advantageous since the specific porosity of this catalyst exhibits a high cycle time in the catalysis of the reaction for the cyclizing hydrolysis of aminonitriles, as is described in patent application WO 96/22974. The presence of the oxygenated compounds mentioned above at the surface of the pores makes it possible to have a better catalytic effect than that with the catalyst prepared with the same oxygenated compound but in unsupported, bulk form. When the inorganic oxide forming the support has catalytic activity in the cyclizing hydrolysis reaction, the presence of these oxidized compounds modifies the catalytic activity of the catalyst by in particular improving the selectivity of the reaction, by minimizing the side reactions.

According to another characteristic of the invention, the efficacy of the catalyst, and more particularly its selectivity, can be improved by the presence, with the oxygenated compound, of anions chosen from the group comprising fluorine, anions of general formula (MxOy) in which M represents an element chosen from the group comprising silicon, arsenic, antimony, nitrogen, sulphur, carbon and phosphorus, x being an integer between 1 and 4 and y being an integer between 1 and 8, or heteropolyanions (HPA) of general formula $X^{(n+)}T_{12}O_{40}^{(6-n)-}$ in which T is tungsten or molybdenum and X is silicon, germanium, phosphorus, arsenic or vanadium.

As examples of anions which are more particularly suitable for the invention, mention may be made in particular of phosphates, sulphates, silicates and the dodecamolybdate and dodecatungstate heteropolyanions.

Consequently, the crude lactam obtained is of better quality. The production of a purified lactam which satisfies the specifications mentioned above is made easier.

The weight concentration of oxygenated compound present in the catalyst is advantageously between 1000 ppm and 30% expressed as mass of element in the oxygenated compound relative to the total mass of the catalyst. This concentration is more preferably between 0.5% and 15% by weight.

The concentration of anions present in the catalyst is advantageously between 0.5 and 15% by weight.

When the porous supports correspond to aluminas in accordance with the invention, these aluminas are generally obtained by dehydration of gibbsite, bayerite, nordstrandite or various mixtures thereof. The various processes for preparing aluminas are described in the Kirk-Othmer encyclopaedia, Volume 2, pages 291–297.

The aluminas used in the present process can be prepared by placing a hydrated alumina, in finely divided form, in contact with a hot stream of gas at a temperature between 400° C. and 1000° C., followed by maintaining the contact between the hydrate and the gases for a period ranging from a fraction of a second up to 10 seconds, and finally separation of the partially dehydrated alumina and the hot gases. Reference may be made in particular to the process described in U.S. Pat. No. 2,915,365.

It is also possible to carry out the autoclaving of alumina agglomerates obtained above, in aqueous medium, optionally in the presence of acid, at a temperature above 100° C. and preferably between 150° C. and 250° C., for a period preferably of between 1 and 20 hours, followed by drying and calcining them.

The calcination temperature is adjusted such that specific surfaces and pore volumes within the range of values indicated above, are obtained.

The catalysts of the invention advantageously have a specific surface of greater than 50 m$^2$/g.

In addition, they advantageously have pores greater than 0.1 μm in diameter, the pore volume provided by these pores being greater than or equal to 5 ml/100 g, advantageously greater than or equal to 10 ml/100 g.

In one preferred embodiment of the invention, these catalysts also comprise pores greater than or equal to 0.5 μm in diameter, the corresponding pore volume being greater than or equal to 5 ml/100 g, preferably greater than or equal to 10 ml/100 g.

This pore volume generated by the pores greater than 500 Å in diameter, preferably greater than 0.1 μm and advantageously greater than 0.5 μm, makes it possible to obtain catalysts with a high cycle time as catalyst for the cyclizing hydrolysis reaction of aminonitriles into lactams. Thus, such catalysts can be used in industrial processes for the production of lactams.

According to the invention, the catalysts comprising oxygenated compounds supported by a porous support are obtained, generally by impregnation of the support, in particular alumina, with a solution of a salt or compounds of the elements mentioned above, and are then dried and calcined at a temperature greater than or equal to 400° C., in order optionally and advantageously to convert the said compounds or salts into oxygenated compounds, preferably into oxides.

Similarly, addition of the anions can be carried out by placing the porous support in contact, before impregnation with the oxygenated compounds or together with this impregnation, with a solution containing salts based on these anions which are advantageously thermally decomposable, such as ammonium salts. This addition can also be performed by placing the porous catalyst comprising the oxygenated compound in contact with a solution containing the anion to be added.

The oxides and the anions are generally present at the surface of the pores of the support by these embodiments.

In another embodiment already mentioned above, the compounds of elements can be added to the material constituting the support before shaping it or during the shaping process.

Calcination of the impregnated supports is preferably performed under an oxidizing atmosphere such as air.

Thus, as will be demonstrated below, the cyclizing hydrolysis reaction can be performed with a minimum of side reactions, thus substantially improving the selectivity of the process towards lactam and hence the purity of the crude product obtained.

The cyclizing hydrolysis reaction requires the presence of water. The molar ratio between the water and the aminonitrile used is usually between 0.5 and 50 and preferably between 1 and 20. The upper value of this ratio is not critical for the invention, but higher ratios are of little interest on economic grounds.

The aminonitrile and the water can be used in the form of their mixtures in vapour form.

In another embodiment, the aminonitrile and water reagents are used in liquid form under pressure, optionally in the presence of a solvent.

In the preferred mode of the invention, the reagents are maintained in vapour form in the reactor charged with a predetermined amount of catalyst.

The free volume of the reactor can be occupied by an inert solid such as, for example, quartz, in order to promote the vaporization and dispersion of the reagents.

It is possible, without inconvenience, to use any inert gas as vector, such as nitrogen, helium or argon.

The temperature at which the process of the invention is carried out must be sufficient for the reagents to be correctly in vapour form. It is generally between 200° C. and 450° C. and preferably between 250° C. and 400° C.

The contact time between the aminonitrile and the catalyst is not critical. This contact time is preferably between 0.5 and 200 seconds and more preferably between 1 and 100 seconds.

The pressure is not a critical parameter of the process. Thus, the process can be performed under pressures from $10^{-3}$ bar to 200 bar. Preferably, the process will be performed under a pressure from 0.1 to 20 bar. In the case of a hydrolysis performed in the vapour phase, this pressure is advantageously between $10^{-3}$ bar and 3 bar.

It is not excluded to use an inert solvent under the reaction conditions, such as, for example, an alkane, a cycloalkane, an aromatic hydrocarbon or a halogenated form of one of the above hydrocarbons, and thus to have a liquid phase in the reaction flow.

The aminonitriles which can be cyclized by the process of the invention are advantageously aliphatic ω-aminonitriles such as ω-aminovaleronitrile, ω-aminocapronitrile, ω-aminooctanitrile, ω-aminononanitrile, ω-aminodecanitrile, ω-aminodecanonitrile, ω-aminododecanonitrile or methylaminovaleronitrile.

The preferred and most important compound is aminocapronitrile, which gives ε-caprolactam. The latter compound is the monomer of polyamide 6 used for the manufacture of various articles such as moulded components, yarns, fibres, filaments, cables or films.

The ε-caprolactam produced by the cyclizing hydrolysis reaction is advantageously purified by the various known purification processes, such as distillation, crystallization in solvent medium or in molten phase, treatment on resin, treatment with an oxidizing agent and/or hydrogenation. These various steps can be partially or totally combined in different orders and depending on the degree of purity of the ε-caprolactam produced.

One of the advantages of the invention lies in the simplification of the purification process, by involving only one or two of these steps.

Other aims, advantages and details will emerge more clearly in the light of the examples given below, purely for indicative purposes.

EXAMPLES 1 TO 3

200 g of catalyst are loaded and distributed into a cylindrical reactor 40 mm in diameter and equal to 1 m in height, in the following way:

in a first section of reactor, 43.7 g of catalyst are mixed with 889 g of glass beads, in a second section of the reactor, 156.3 g of catalyst are mixed with 169 g of glass beads.

Water and aminocapronitrile are injected at mass flow rates equal to 129 g/h and 200 g/h, respectively.

The reactor is maintained at a temperature of 300° C.

The test is stopped after an operating time of 500 hours.

The reaction mixture is assayed by gas chromatography, in particular to determine the caprolactam concentration.

The degree of conversion (DC) of the aminocapronitrile and the selectivity S towards caprolactam (CPL) relative to the aminocapronitrile converted are determined.

The quality of the crude caprolactam obtained is measured by titration of a sulphuric caprolactam solution with aqueous 0.2 N potassium permanganate solution. It is expressed in ml of $KMnO_4$ solution per kg of caprolactam.

This assay is carried out according to the following procedure:

3 g of a solution containing the caprolactam whose caprolactam concentration has been determined by liquid chromatography are added to 60 ml of water. 3 ml of concentrated (98%) sulphuric acid solution are added to the caprolactam solution. The permanganate index, determined after neutralization of the medium at a pH of 7, is measured by addition of 0.2 N potassium permanganate solution.

The alumina used as catalyst has the following properties:
Alumina:
specific surface (SS): 139 $m^2/g$
total pore volume: 117 ml/100 g
pore volume corresponding to pores greater than 500 Å in diameter: 50 ml/100 g
pore volume corresponding to pores greater than 200 Å in diameter: 70 ml/100 g
pore volume corresponding to pores greater than 70 Å in diameter: 116 ml/100 g.

The table below collates the results obtained in:
Example 1, which is representative of the prior art (patent application Wo 96/22974) and was performed with the alumina described above;
Examples 2 and 3 are representative of the invention; they were performed with catalysts made, respectively, by impregnation, drying and calcination of 3% $TiO_2$ and 3% $La_2O_3$ deposited on the alumina described above.

TABLE I

| Examples | | 1 | 2 | 3 |
|---|---|---|---|---|
| Catalyst | | Alumina | Alumina + 3% $TiO_2$ | Alumina + 3% $La_2O_3$ |
| After 500 hours | DC of ACN | 96.3% | 97.1 | 96.5 |
| | S of CPL | >99% | >99% | >99% |
| | Quality of the crude CPL (ml $KMnO_4$ /kg CPL) | 123 | 62 | 91 |

EXAMPLES 4 TO 11

166.5 g of catalyst are loaded and distributed into a cylindrical reactor 40 mm in diameter and equal to 1 m in height, in the following manner:
in a first section of reactor, 36.5 g of catalyst are mixed with 845 g of glass beads,
in a second section of the reactor, 130 g of catalyst without glass beads.

Water and aminocapronitrile are injected at mass flow rates equal to 128 g/h and 200 g/h, respectively.

The reactor is maintained at a temperature of 300° C.
The test is stopped after an operating time of 200 hours.
The reaction mixture is assayed by gas chromatography, in particular in order to determine the caprolactam concentration.

The degree of conversion (DC) of the aminocapronitrile and the selectivity S towards caprolactam (CPL) relative to the aminocapronitrile converted are determined.

The quality of the crude caprolactam contained in the reaction medium is assessed by measuring the permanganate index, determined by neutralization of the medium to a pH of 7 by addition of hydrochloric acid solution and measurement of the UV absorbance at a wavelength of 290 nm. This quality is also characterized by determining the polarographic index, known as IPOL, which is representative of the concentration of electroreducible imines in the medium analysed.

This index is determined according to the following procedure:

The electrolyte (a 10% by weight solution of HMD in water) is introduced into a polarographic vessel 10 or 20 ml in volume. After de-aeration with stirring, the electrolyte is subjected to a flow of argon or nitrogen for 5 minutes.

A polarogram "blank" is produced under a nitrogen or argon atmosphere.

0.1 g of sample to be analysed is added to this electrolyte. After de-aeration and passage under an inert nitrogen or argon atmosphere, a "blank+sample" polarogram is established.

A standard isobutanal sample containing 500 mg of isobutanal in methanol, the volume of solution being 50 ml, is added to the electrolyte+sample medium. A polarogram is established under the same conditions as above.

The polarograms are recorded under the following conditions:
initial potential=−1.1 V/Ag—AgCl
final potential=−1.9 V/Ag—AgCl
sweep speed=4 mV/s
Calculation of the IPOL index is given by the formula:

$$IPOL = \frac{10^8}{72.11} \times \frac{V \times U}{M^1} \times \frac{I_2 - I_1}{I_3 - I_2}$$

in which:
$M^1$ represents the mass in grams of the sample taken of the medium to be analysed,
$I_1$ represents the reduction current corresponding to the electrolyte "blank" in nA, measured at −1.7 V/Ag—AgCl,
$I_2$ represents the reduction current corresponding to the "blank+sample", measured at −1.7 V/Ag—AgCl,
$I_3$ represents the reduction current corresponding to the "blank+sample+standard", measured at −1.7 V/Ag—AgCl,
V represents the volume in ml of the standard added,
U represents the titre in g/l of isobutanal in the standard solution,
IPOL is the polarographic index of the imines, expressed in mmol of isobutanal/tonne of sample.

The alumina used as catalyst has the following properties:
specific surface (SS): 140 $m^2/g$
total pore volume: 112.9 ml/100 g
pore volume corresponding to pores greater than 10,000 Å in diameter: 12 ml/100 g
pore volume corresponding to pores greater than 1000 Å in diameter: 34.8 ml/100 g
pore volume corresponding to pores greater than 200 Å in diameter: 92 ml/100 g
pore volume corresponding to pores greater than 70 Å in diameter: 111 ml/100 g.

Table II below collates the results obtained.
Comparative Example 4 was carried out with the above alumina as catalyst, free of oxidized compounds and/or of anions,
Examples 5 to 11 are representative of the invention. They were performed with catalysts obtained by impregnation of the abovementioned alumina with a precursor of oxygenated elements, drying and calcination. The composition of the catalysts tested is indicated in Table II below.

This Table II also collates the results obtained regarding the activity of the catalyst in terms of degree of conversion of the ACN and selectivity towards caprolactam.

The results regarding the quality of the caprolactam obtained are collated in Table III. These results clearly show the effects of the presence of these oxygenated elements at the surface of the porous support both on the imine content (IPOL index) and on the permanganate index and UV absorbance.

Consequently, the invention makes it possible to produce a purer caprolactam which may be purified more easily and with fewer elemental purification steps to satisfy the specifications required for its use, in particular for the manufacture of polyamide for textile use.

TABLE II

| Example No. | Catalyst (mol % of the element relative to the weight of the catalyst) | DC (ACN) in % | S (CPL) in % |
| --- | --- | --- | --- |
| 4 | $Al_2O_3$ | 99.1 | 99.8 |
| 5 | $Al_2O_3$, Fe (3%) | 99.4 | 99.9 |
| 6 | $Al_2O_3$, P (3%) | 99.4 | 99.9 |
| 7 | $Al_2O_3$, Ti (3%) | 99.6 | 99.9 |
| 8 | $Al_2O_3$, Ti (8%) | 99.7 | 99.5 |
| 9 | $Al_2O_3$, Sn (3%) | 99.7 | 99.7 |
| 10 | $Al_2O_3$, V (3%) | 99.5 | 99.9 |
| 11 | $Al_2O_3$, W (3%) | 99.4 | 100 |
| 12 | $Al_2O_3$, Ti (1.5%) Fe (1.5%) | 99.7 | 100 |

TABLE III

| Example No. | IPOL | $KMnO_4$ index | Absorbance at 290 nm |
| --- | --- | --- | --- |
| 4 | 4200 | 409 | 1.9 |
| 5 | 990 | 235 | 1.0 |
| 6 | 1105 | 299 | 1.4 |
| 7 | 2425 | 271 | 1.5 |
| 8 | 2235 | 172 | 2.0* |
| 9 | 3133 | 238 | 1.65 |
| 10 | 1545 | 251 | 1.5 |
| 11 | 715 | 293 | 1.2 |
| 12 | 1860 | 111 | 0.9 |

What is claimed is:

1. A process for the cyclizing hydrolysis of an aminonitrile compound into a lactam, comprising reacting an aminonitrile of formula (I):

$$N\equiv C-R-NH_2 \qquad (I)$$

in which R represents a substituted or unsubstituted aliphatic, cycloaliphatic or arylaliphatic radical comprising from 3 to 12 carbon atoms, with water, in the presence of a solid catalyst, wherein the catalyst is a particulate catalyst obtained by deposition and/or adsorption of at least one oxygenated compound of at least one element selected from the group consisting of the elements belonging to groups 1 to 16 of the universal classification of the elements, said list further comprising rare-earth metals, on a support made of simple or mixed inorganic oxide or a mixture of oxides of at least one element selected from the group consisting of silicon, aluminium, titanium, zirconium, vanadium, niobium, tantalum, tungsten, molybdenum, iron and rare-earth metals, and comprising at least one macroporosity having a pore volume, corresponding to pores greater than 500 Å in diameter, of greater than or equal to 5 ml/100 g.

2. The process according to claim 1, wherein the particulate catalyst has a specific surface of greater than 10 $m^2/g$ and a total pore volume of greater than or equal to 10 ml/100 g, the pore volume corresponding to pores greater than 500 Å in diameter being greater than or equal to 10 ml/100 g.

3. The process according to claim 1, wherein the catalyst has a specific surface of greater than 50 $m^2/g$.

4. The process according to claim 1, wherein the catalyst has a total pore volume of greater than or equal to 20 ml/100 g with a pore volume corresponding to pores greater than 70 Å in diameter of greater than or equal to 20 ml/100 g.

5. The process according to claim 1, wherein the catalyst has a total pore volume of greater than or equal to 15 ml/100 g with a pore volume corresponding to pores greater than 200 Å in diameter of greater than or equal to 15 ml/100 g.

6. The process according to claim 1, wherein the oxygenated compounds supported on a porous support are oxygenated compounds of elements selected from the group consisting of silicon, titanium, zirconium, vanadium, niobium, tantalum, tungsten, molybdenum, hafnium, scandium, phosphorus, boron, iron, alkaline-earth metals and rare-earth metals or mixtures thereof or mixed oxides.

7. The process according to claim 1, wherein the catalyst comprises anions selected from the group consisting of fluorine, anions of formula (MxOy) in which M represents an element selected from the group consisting of silicon, arsenic, antimony, nitrogen, sulphur, carbon and phosphorus, x being an integer between 1 and 4 and y being an integer between 1 and 8, or heteropolyanions (HPA) of general formula $X^{(n+)}T_{12}O_{40}^{(6-n)-}$ in which T is tungsten or molybdenum and X is silicon, germanium, phosphorus, arsenic or vanadium.

8. The process according to claim 1, wherein the concentration of oxygenated compounds, expressed by weight of element relative to the weight of catalyst, is between 1000 ppm and 30%.

9. The process according to claim 8, wherein the concentration of oxygenated compounds is between 0.5% and 15% by weight relative to the weight of catalyst.

10. The process according to claim 7, wherein the concentration of anions is between 0.5 and 15% by weight relative to the weight of catalyst.

11. The process according to one of the claim 1, wherein the particulate catalyst is in the form of beads, crushings, extrudates in the form of cylindrical granules or in hollow or solid multilobe form or in the form of honeycombs or pellets.

12. The process according to claim 1, wherein the porous support is alumina.

13. The process according to claim 1, wherein the cyclizing hydrolysis reaction is carried out in the vapor phase.

* * * * *